(12) United States Patent
Luo et al.

(10) Patent No.: US 12,595,308 B2
(45) Date of Patent: Apr. 7, 2026

(54) ANTI-B7H3 ANTIBODY AND USE THEREOF

(71) Applicant: GUANGZHOU BIO-GENE TECHNOLOGY CO., LTD, Guangdong (CN)

(72) Inventors: Min Luo, Guangdong (CN); Guangchao Li, Guangdong (CN); Zhao Zhou, Guangdong (CN); Xuejun Wang, Guangdong (CN)

(73) Assignee: GUANGZHOU BIO-GENE TECHNOLOGY CO., LTD, Guangdong (CN)

( * ) Notice: Subject to any disclaimer, the term of this patent is extended or adjusted under 35 U.S.C. 154(b) by 229 days.

(21) Appl. No.: 18/003,996

(22) PCT Filed: Dec. 15, 2020

(86) PCT No.: PCT/CN2020/136409
§ 371 (c)(1),
(2) Date: Dec. 30, 2022

(87) PCT Pub. No.: WO2022/001020
PCT Pub. Date: Jan. 6, 2022

(65) Prior Publication Data
US 2025/0011430 A1    Jan. 9, 2025

(30) Foreign Application Priority Data
Jun. 30, 2020    (CN) ......................... 202010622482.X

(51) Int. Cl.
*C07K 16/28* (2006.01)
*C12N 15/63* (2006.01)
*A61K 39/00* (2006.01)

(52) U.S. Cl.
CPC .......... *C07K 16/2827* (2013.01); *C12N 15/63* (2013.01); *A61K 2039/505* (2013.01); *C07K 2317/41* (2013.01); *C07K 2317/52* (2013.01); *C07K 2317/565* (2013.01)

(58) Field of Classification Search
None
See application file for complete search history.

(56) References Cited

U.S. PATENT DOCUMENTS

2017/0355769 A1*  12/2017  Benatuil ................. A61P 35/00
2017/0362322 A1   12/2017  DuBridge et al.

FOREIGN PATENT DOCUMENTS

| CN | 101104639 | 1/2008 |
|----|-----------|--------|
| CN | 103687945 | 3/2014 |
| CN | 109563167 | 4/2019 |
| CN | 110799542 | 2/2020 |
| CN | 111662384 | 9/2020 |
| JP | 2016088886 | 5/2016 |
| WO | 2007/008527 | 1/2007 |
| WO | 2008/116219 | 9/2008 |
| WO | 2011/109400 | 9/2011 |
| WO | 2016/033225 | 3/2016 |
| WO | 2016/106004 | 6/2016 |
| WO | 2020/063673 | 4/2020 |
| WO | 2020/076970 | 4/2020 |

OTHER PUBLICATIONS

Office Action (and corresponding translation) mailed on Dec. 15, 2020 for CN Application No. 202010622482.X.
Office Action (and corresponding translation) mailed on Aug. 18, 2023 for CN Application No. 202110213973.3.
Office Action (and corresponding translation) mailed on Sep. 1, 2021 for CN Application No. 202110214987.7.
Office Action (and corresponding translation) mailed on Nov. 17, 2021 for CN Application No. 202110213973.3.
Office Action (and corresponding translation) mailed on Jul. 7, 2021 for CN Application No. 202110213393.4.
Yan et al., "A Novel Monoclonal Antibody Against Mouse B7-H3 Developed in Rats," (2012) Hybridoma 31(4):267-271.
GenBank Accession No. BAC56972.1, "Anti-Glycyrrhetic Acid Antibody GA007 Light Chain, Partial [Mus Musculus]," available at https://www.ncbi.nlm.nih.gov/nuccore/AB089688.1?from=1&to= 372 (Submitted on Aug. 9, 2002).
Loo et al., "Cancer Therapy: Preclinical, Development of an Fc-Enhanced Anti-B7-H3 Monoclonal Antibody with Potent Antitumor Activity," (2012) Clinic Cancer Research 18(14):3834-3845.
GenBank Accession No. AHK61066.1, "Immunoglobulin Heavy Chain Variable Region, Partial [Mus Musculus]," available at https://www.ncbi.nlm.nih.gov/protein/AHK61066.1 (Submitted on Dec. 11, 2013).
GenBank Accession No. AHK61072.1, "Immunoglobulin Heavy Chain Variable Region, Partial [Mus Musculus]," available at_https:// www.ncbi.nlm.nih.gov/protein/AHK61072.1 (Submitted Dec. 11, 2013).
Luther et al., "Interstitial Infusion of Glioma-Targeted Recombinant Immunotoxin 8H9scFv-PE38," (2010) Molecular Cancer Therapeutics 9(4):1039-1046.
Picarda et al., "Molecular Pathways: Targeting B7-H3 (CD276) for Human Cancer Immunotherapy," (2016) Clinical Cancer Research 22(14):1-20.

(Continued)

*Primary Examiner* — Laura B Goddard
(74) *Attorney, Agent, or Firm* — Jenkins, Taylor & Hunt, P.A.

(57) ABSTRACT

Provided are an anti-B7H3 antibody and the use thereof. A variable region of the antibody comprises amino acid sequences as shown in SEQ ID NOs: 25-39. The anti-B7H3 antibodies 26B6, 6F7, 2B8, and 23H1 have a significant binding capability to B7H3, can not only bind to purified or free B7H3 protein, but also can bind to B7H3 protein on a cell surface; and after humanized modification, the affinity between the antibody and B7H3 is further improved, and the antibody has important application prospects in clinical diagnosis and/or treatment of B7H3-positive tumors.

11 Claims, 5 Drawing Sheets
Specification includes a Sequence Listing.

(56)          References Cited

OTHER PUBLICATIONS

Rao et al., "Preparation of a Novel Functional Mouse Anti-Human 2IgB7-H3 Antibody and Primary Study of its Biological Characteristics," (2006) Current Immunology (04):278-282.

He et al., "Preparation of a Monoclonal Antibody Against Human 4IgB7-H3 Molecule and Analysis of its Biological Characteristics," (2009) Fundamental Medicine (06):447-452.

International Search Report issued on Mar. 26, 2021 in PCT Application No. PCT/CN2020/136409.

* cited by examiner

SEQUENCE LISTING

```
<160> NUMBER OF SEQ ID NOS: 39

<210> SEQ ID NO 1
<211> LENGTH: 14
<212> TYPE: PRT
<213> ORGANISM: artificial sequence
<220> FEATURE:
<223> OTHER INFORMATION: CDR3

<400> SEQUENCE: 1

Pro Tyr Arg Asp Asp Gly Gly Phe His Trp Tyr Phe Asp Val
1               5                   10

<210> SEQ ID NO 2
<211> LENGTH: 9
<212> TYPE: PRT
<213> ORGANISM: artificial sequence
<220> FEATURE:
<223> OTHER INFORMATION: CDR3

<400> SEQUENCE: 2

Asp Ser His Tyr Arg Pro Phe Ala Tyr
1               5

<210> SEQ ID NO 3
<211> LENGTH: 13
<212> TYPE: PRT
<213> ORGANISM: artificial sequence
<220> FEATURE:
<223> OTHER INFORMATION: CDR3

<400> SEQUENCE: 3

Gly Val Phe Tyr Tyr Gly Tyr Gly Ala Trp Phe Ala Tyr
1               5                   10

<210> SEQ ID NO 4
<211> LENGTH: 9
<212> TYPE: PRT
<213> ORGANISM: artificial sequence
<220> FEATURE:
<223> OTHER INFORMATION: CDR3

<400> SEQUENCE: 4

Asp Ser Pro Tyr Arg Pro Phe Ala Tyr
1               5

<210> SEQ ID NO 5
<211> LENGTH: 9
<212> TYPE: PRT
<213> ORGANISM: artificial sequence
<220> FEATURE:
<223> OTHER INFORMATION: CDR3

<400> SEQUENCE: 5

Gln Gln Trp Ser Ser Asn Pro Leu Thr
```

```
1                5
```

```
<210> SEQ ID NO 6
<211> LENGTH: 9
<212> TYPE: PRT
<213> ORGANISM: artificial sequence
<220> FEATURE:
<223> OTHER INFORMATION: CDR3

<400> SEQUENCE: 6

Gln Asn Asp Tyr Thr Tyr Pro Leu Thr
1                5

<210> SEQ ID NO 7
<211> LENGTH: 9
<212> TYPE: PRT
<213> ORGANISM: artificial sequence
<220> FEATURE:
<223> OTHER INFORMATION: CDR3

<400> SEQUENCE: 7

Gln Gln His His Glu Tyr Pro Leu Thr
1                5

<210> SEQ ID NO 8
<211> LENGTH: 8
<212> TYPE: PRT
<213> ORGANISM: artificial sequence
<220> FEATURE:
<223> OTHER INFORMATION: CDR3

<400> SEQUENCE: 8

Asn Asp Tyr Thr Tyr Pro Leu Thr
1                5

<210> SEQ ID NO 9
<211> LENGTH: 6
<212> TYPE: PRT
<213> ORGANISM: artificial sequence
<220> FEATURE:
<223> OTHER INFORMATION: CDR2

<400> SEQUENCE: 9

Asn Pro Asn Thr Gly Gly
1                5

<210> SEQ ID NO 10
<211> LENGTH: 8
<212> TYPE: PRT
<213> ORGANISM: artificial sequence
<220> FEATURE:
<223> OTHER INFORMATION: CDR2

<400> SEQUENCE: 10

Arg Asn Lys Ala Asn Gly Tyr Thr
1                5

<210> SEQ ID NO 11
<211> LENGTH: 6
<212> TYPE: PRT
<213> ORGANISM: artificial sequence
<220> FEATURE:
<223> OTHER INFORMATION: CDR2

<400> SEQUENCE: 11

Asn Thr Asn Ser Gly Asn
1                5
```

-continued

```
<210> SEQ ID NO 12
<211> LENGTH: 8
<212> TYPE: PRT
<213> ORGANISM: artificial sequence
<220> FEATURE:
<223> OTHER INFORMATION: CDR2

<400> SEQUENCE: 12

Arg Asn Lys Val Asn Asp Tyr Thr
1               5

<210> SEQ ID NO 13
<211> LENGTH: 7
<212> TYPE: PRT
<213> ORGANISM: artificial sequence
<220> FEATURE:
<223> OTHER INFORMATION: CDR2

<400> SEQUENCE: 13

Asp Thr Ser Lys Leu Thr Ser
1               5

<210> SEQ ID NO 14
<211> LENGTH: 7
<212> TYPE: PRT
<213> ORGANISM: artificial sequence
<220> FEATURE:
<223> OTHER INFORMATION: CDR2

<400> SEQUENCE: 14

Leu Ala Ser Thr Arg Asp Ser
1               5

<210> SEQ ID NO 15
<211> LENGTH: 7
<212> TYPE: PRT
<213> ORGANISM: artificial sequence
<220> FEATURE:
<223> OTHER INFORMATION: CDR2

<400> SEQUENCE: 15

Ser Gly Ser Thr Leu Gln Ser
1               5

<210> SEQ ID NO 16
<211> LENGTH: 7
<212> TYPE: PRT
<213> ORGANISM: artificial sequence
<220> FEATURE:
<223> OTHER INFORMATION: CDR2

<400> SEQUENCE: 16

Leu Ala Ser Thr Arg Glu Ser
1               5

<210> SEQ ID NO 17
<211> LENGTH: 7
<212> TYPE: PRT
<213> ORGANISM: artificial sequence
<220> FEATURE:
<223> OTHER INFORMATION: CDR1

<400> SEQUENCE: 17

Gly Tyr Ala Phe Thr Glu Tyr
1               5
```

```
<210> SEQ ID NO 18
<211> LENGTH: 7
<212> TYPE: PRT
<213> ORGANISM: artificial sequence
<220> FEATURE:
<223> OTHER INFORMATION: CDR1

<400> SEQUENCE: 18

Gly Phe Thr Phe Thr Asp Tyr
1               5

<210> SEQ ID NO 19
<211> LENGTH: 7
<212> TYPE: PRT
<213> ORGANISM: artificial sequence
<220> FEATURE:
<223> OTHER INFORMATION: CDR1

<400> SEQUENCE: 19

Gly Tyr Thr Phe Thr Asp Gly
1               5

<210> SEQ ID NO 20
<211> LENGTH: 7
<212> TYPE: PRT
<213> ORGANISM: artificial sequence
<220> FEATURE:
<223> OTHER INFORMATION: CDR1

<400> SEQUENCE: 20

Gly Phe Thr Phe Thr Asp Tyr
1               5

<210> SEQ ID NO 21
<211> LENGTH: 10
<212> TYPE: PRT
<213> ORGANISM: artificial sequence
<220> FEATURE:
<223> OTHER INFORMATION: CDR1

<400> SEQUENCE: 21

Ser Ala Ser Ser Ser Val Ser Tyr Met Gln
1               5                   10

<210> SEQ ID NO 22
<211> LENGTH: 17
<212> TYPE: PRT
<213> ORGANISM: artificial sequence
<220> FEATURE:
<223> OTHER INFORMATION: CDR1

<400> SEQUENCE: 22

Lys Ser Ser Gln Ser Leu Leu Asn Ser Gly Asn Gln Asn Asn Tyr Leu
1               5                   10                  15

Thr

<210> SEQ ID NO 23
<211> LENGTH: 11
<212> TYPE: PRT
<213> ORGANISM: artificial sequence
<220> FEATURE:
<223> OTHER INFORMATION: CDR1

<400> SEQUENCE: 23

Arg Ala Ser Lys Thr Ile Ser Asn Tyr Leu Ala
1               5                   10
```

```
<210> SEQ ID NO 24
<211> LENGTH: 17
<212> TYPE: PRT
<213> ORGANISM: artificial sequence
<220> FEATURE:
<223> OTHER INFORMATION: CDR1

<400> SEQUENCE: 24

Lys Ser Ser Gln Thr Leu Leu Asn Asn Gly Asn Gln Lys Asn Phe Leu
1               5                   10                  15

Thr

<210> SEQ ID NO 25
<211> LENGTH: 125
<212> TYPE: PRT
<213> ORGANISM: artificial sequence
<220> FEATURE:
<223> OTHER INFORMATION: 26B6HV

<400> SEQUENCE: 25

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ala Phe Thr Glu Tyr
            20                  25                  30

Thr Met His Trp Val Lys Gln Ser Gln Gly Lys Ser Leu Glu Trp Ile
        35                  40                  45

Gly Gly Ile Asn Pro Asn Thr Gly Gly Thr Thr Tyr Asn Gln Lys Phe
    50                  55                  60

Asn Gly Lys Ala Thr Leu Thr Val Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Pro Tyr Arg Asp Asp Gly Gly Phe His Trp Tyr Phe Asp Val
            100                 105                 110

Trp Gly Ala Gly Thr Ala Val Thr Val Ser Ser Ala Ser
        115                 120                 125

<210> SEQ ID NO 26
<211> LENGTH: 112
<212> TYPE: PRT
<213> ORGANISM: artificial sequence
<220> FEATURE:
<223> OTHER INFORMATION: 26B6LV

<400> SEQUENCE: 26

Gln Ile Val Leu Thr Gln Ser Pro Ala Val Met Ser Thr Ser Pro Gly
1               5                   10                  15

Glu Lys Val Thr Met Thr Cys Ser Ala Ser Ser Ser Val Ser Tyr Met
            20                  25                  30

Gln Trp Tyr Gln Gln Lys Ser Gly Thr Ser Pro Lys Arg Trp Ile Tyr
        35                  40                  45

Asp Thr Ser Lys Leu Thr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
```

-continued

```
              100            105            110

<210> SEQ ID NO 27
<211> LENGTH: 123
<212> TYPE: PRT
<213> ORGANISM: artificial sequence
<220> FEATURE:
<223> OTHER INFORMATION: hz26B6HV

<400> SEQUENCE: 27

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Ile
        35                  40                  45

Gly Gly Ile Asn Pro Asn Thr Gly Gly Thr Thr Tyr Asn Gln Lys Phe
    50                  55                  60

Asn Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Pro Tyr Arg Asp Asp Gly Gly Phe His Trp Tyr Phe Asp Val
            100                 105                 110

Trp Gly Gln Gly Thr Leu Val Thr Val Ser Ser
        115                 120

<210> SEQ ID NO 28
<211> LENGTH: 109
<212> TYPE: PRT
<213> ORGANISM: artificial sequence
<220> FEATURE:
<223> OTHER INFORMATION: hz26B6LV

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
                20                  25                  30

Gln Trp Tyr Gln Gln Lys Pro Gly Leu Ala Pro Arg Leu Leu Ile Tyr
        35                  40                  45

Asp Thr Ser Lys Leu Thr Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Arg Thr Val
            100                 105

<210> SEQ ID NO 29
<211> LENGTH: 122
<212> TYPE: PRT
<213> ORGANISM: artificial sequence
<220> FEATURE:
<223> OTHER INFORMATION: 6F7HV

<400> SEQUENCE: 29

Glu Val Lys Leu Val Glu Ser Gly Gly Gly Leu Val Gln Pro Gly Gly
1               5                   10                  15
```

-continued

Ser Leu Arg Leu Ser Cys Ala Thr Ser Gly Phe Thr Phe Thr Asp Tyr
        20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Ser Asp Asp Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Ser His Tyr Arg Pro Phe Ala Tyr Trp Gly Gln
            100                 105                 110

Gly Thr Leu Val Thr Val Ser Ala Ala Ser
        115                 120

<210> SEQ ID NO 30
<211> LENGTH: 119
<212> TYPE: PRT
<213> ORGANISM: artificial sequence
<220> FEATURE:
<223> OTHER INFORMATION: 6F7LV

<400> SEQUENCE: 30

Asp Ile Gln Met Thr Gln Ser Pro Ser Ser Leu Thr Val Thr Ala Gly
1                   5                   10                  15

Glu Lys Val Thr Met Ser Cys Lys Ser Ser Gln Ser Leu Leu Asn Ser
        20                  25                  30

Gly Asn Gln Asn Asn Tyr Leu Thr Trp Tyr Gln Gln Lys Pro Gly Gln
        35                  40                  45

Pro Pro Lys Leu Leu Ile Tyr Leu Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Leu Thr Phe Gly Ala Gly Thr Lys Leu Glu Leu
            100                 105                 110

Lys Arg Ala Asp Ala Ala Pro
        115

<210> SEQ ID NO 31
<211> LENGTH: 120
<212> TYPE: PRT
<213> ORGANISM: artificial sequence
<220> FEATURE:
<223> OTHER INFORMATION: hz6F7HV

<400> SEQUENCE: 31

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Thr Asp Tyr
        20                  25                  30

Tyr Met Ser Trp Val Arg Gln Ala Pro Gly Lys Gly Leu Glu Trp Val
        35                  40                  45

Ala Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asp Ser Lys Asn Ser

```
65                  70                  75                  80

Leu Tyr Leu Gln Met Asn Ser Leu Arg Ala Glu Asp Thr Ala Val Tyr
                85                  90                  95

Tyr Cys Ala Arg Asp Ser His Tyr Arg Pro Phe Ala Tyr Trp Gly Gln
            100                 105                 110

Gly Thr Leu Val Thr Val Ser Ser
        115                 120

<210> SEQ ID NO 32
<211> LENGTH: 116
<212> TYPE: PRT
<213> ORGANISM: artificial sequence
<220> FEATURE:
<223> OTHER INFORMATION: hz6F7LV1

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asn Ser
            20                  25                  30

Gly Asn Gln Asn Asn Tyr Leu Thr Trp Tyr Leu Gln Lys Pro Gly Gln
        35                  40                  45

Ser Pro Gln Leu Leu Ile Tyr Leu Ala Ser Thr Arg Asp Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Thr Tyr Pro Leu Thr Phe Gly Gly Gly Thr Lys Val Glu Ile
            100                 105                 110

Lys Arg Thr Val
        115

<210> SEQ ID NO 33
<211> LENGTH: 116
<212> TYPE: PRT
<213> ORGANISM: artificial sequence
<220> FEATURE:
<223> OTHER INFORMATION: hz6F7LV2

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Asn Asn Tyr Leu Thr Trp Tyr Gln Gln Lys Pro Gly Gln
        35                  40                  45

Pro Pro Lys Leu Leu Ile Tyr Leu Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Leu Thr Phe Gly Gly Gly Thr Lys Val Glu Ile
            100                 105                 110

Lys Arg Thr Val
        115
```

-continued

<210> SEQ ID NO 34
<211> LENGTH: 124
<212> TYPE: PRT
<213> ORGANISM: artificial sequence
<220> FEATURE:
<223> OTHER INFORMATION: 2B8HV

<400> SEQUENCE: 34

Gln Val Gln Leu Gln Gln Ser Gly Pro Glu Leu Val Arg Pro Gly Val
1               5                   10                  15

Ser Val Lys Ile Ser Cys Lys Val Ser Gly Tyr Thr Phe Thr Asp Gly
            20                  25                  30

Ala Met His Trp Val Lys Arg Ser His Ala Lys Ser Leu Glu Trp Ile
        35                  40                  45

Gly Ile Ile Asn Thr Asn Ser Gly Asn Thr Asn Tyr Asn Gln Lys Phe
    50                  55                  60

Gln Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Val Phe Tyr Tyr Gly Tyr Gly Ala Trp Phe Ala Tyr Trp
            100                 105                 110

Gly Gln Gly Thr Leu Val Thr Val Ser Ala Ala Ser
        115                 120

<210> SEQ ID NO 35
<211> LENGTH: 113
<212> TYPE: PRT
<213> ORGANISM: artificial sequence
<220> FEATURE:
<223> OTHER INFORMATION: 2B8LV

<400> SEQUENCE: 35

Asp Val Gln Ile Thr Gln Ser Pro Ser Tyr Leu Thr Ala Ser Pro Gly
1               5                   10                  15

Glu Thr Ile Ile Ile Asn Cys Arg Ala Ser Lys Thr Ile Ser Asn Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Asp Thr Asp Phe Thr Leu Thr Ile Ser Ser Leu Glu Pro
65                  70                  75                  80

Glu Asp Phe Ala Met Tyr Tyr Cys Gln Gln His His Glu Tyr Pro Leu
                85                  90                  95

Thr Phe Gly Ala Gly Thr Lys Leu Glu Leu Lys Arg Ala Asp Ala Ala
            100                 105                 110

Pro

<210> SEQ ID NO 36
<211> LENGTH: 122
<212> TYPE: PRT
<213> ORGANISM: artificial sequence
<220> FEATURE:
<223> OTHER INFORMATION: hz2B8HV

<400> SEQUENCE: 36

Gln Val Gln Leu Val Gln Ser Gly Ala Glu Val Lys Lys Pro Gly Ala
1               5                   10                  15

-continued

```
Ser Val Lys Val Ser Cys Lys Val Ser Gly Tyr Thr Phe Thr Asp Gly
        20              25              30

Ala Met His Trp Val Arg Gln Ala Pro Gly Gln Gly Leu Glu Trp Ile
        35              40              45

Gly Ile Ile Asn Thr Asn Ser Gly Asn Thr Asn Tyr Asn Gln Lys Phe
    50              55              60

Gln Gly Arg Val Thr Met Thr Arg Asp Thr Ser Ile Ser Thr Ala Tyr
65              70              75              80

Met Glu Leu Ser Arg Leu Arg Ser Glu Asp Thr Ala Val Tyr Tyr Cys
                85              90              95

Ala Arg Gly Val Phe Tyr Tyr Gly Tyr Gly Ala Trp Phe Ala Tyr Trp
            100             105             110

Gly Gln Gly Thr Leu Val Thr Val Ser Ser
        115             120
```

```
<210> SEQ ID NO 37
<211> LENGTH: 110
<212> TYPE: PRT
<213> ORGANISM: artificial sequence
<220> FEATURE:
<223> OTHER INFORMATION: hz2B8LV

<400> SEQUENCE: 37
```

```
Asp Ile Gln Leu Thr Gln Ser Pro Ser Phe Leu Ser Ala Ser Val Gly
1               5               10              15

Asp Arg Val Thr Ile Asn Cys Arg Ala Ser Lys Thr Ile Ser Asn Tyr
        20              25              30

Leu Ala Trp Tyr Gln Gln Lys Pro Gly Lys Ala Pro Lys Leu Leu Ile
        35              40              45

Tyr Ser Gly Ser Thr Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln His His Glu Tyr Pro Leu
                85              90              95

Thr Phe Gly Gly Gly Thr Lys Val Glu Ile Lys Arg Thr Val
            100             105             110
```

```
<210> SEQ ID NO 38
<211> LENGTH: 122
<212> TYPE: PRT
<213> ORGANISM: artificial sequence
<220> FEATURE:
<223> OTHER INFORMATION: 23H1HV

<400> SEQUENCE: 38
```

```
Glu Val Lys Leu Val Glu Ser Gly Gly Gly Leu Val Gln Pro Gly Gly
1               5               10              15

Ser Leu Arg Leu Ser Cys Ala Thr Ser Gly Phe Thr Phe Thr Asp Tyr
        20              25              30

Tyr Met Ser Trp Val Arg Gln Pro Pro Gly Lys Ala Leu Glu Trp Leu
        35              40              45

Gly Phe Ile Arg Asn Lys Val Asn Asp Tyr Thr Thr Glu Tyr Ser Val
    50              55              60

Ser Val Lys Gly Arg Phe Thr Ile Ser Arg Asp Asn Ser Gln Thr Ile
65              70              75              80

Leu Tyr Leu Gln Met Asn Thr Leu Arg Ala Glu Asp Ser Ala Thr Tyr
```

-continued

```
                    85                   90                   95
Tyr Cys Ala Arg Asp Ser Pro Tyr Arg Pro Phe Ala Tyr Trp Gly Gln
                100                 105                 110

Gly Thr Leu Val Thr Val Ser Ala Ala Ser
            115                 120

<210> SEQ ID NO 39
<211> LENGTH: 119
<212> TYPE: PRT
<213> ORGANISM: artificial sequence
<220> FEATURE:
<223> OTHER INFORMATION: 23H1LV

<400> SEQUENCE: 39

Asp Ile Val Met Thr Gln Ser Pro Ser Ser Leu Thr Val Thr Ala Gly
1                 5                  10                  15

Glu Asn Val Thr Met Ser Cys Lys Ser Ser Gln Thr Leu Leu Asn Asn
                20                  25                  30

Gly Asn Gln Lys Asn Phe Leu Thr Trp Tyr Gln Gln Lys Pro Gly Gln
            35                  40                  45

Pro Pro Lys Leu Leu Ile Tyr Leu Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Leu Thr Phe Gly Ala Gly Thr Lys Leu Glu Leu
                100                 105                 110

Lys Arg Ala Asp Ala Ala Pro
            115
```

ANTI-B7H3 ANTIBODY AND USE THEREOF

TECHNICAL FIELD

The present application belongs to the field of biomedical technology and relates to an anti-B7H3 antibody and a use thereof.

BACKGROUND

B7-H3 is a type I transmembrane protein, which belongs to a B7 immune co-stimulation and co-suppression family with two isotypes 2Ig-B7-H3 and 4Ig-B7-H3 in humans and one isotype 2Ig-B7-H3 in mice, where human 2Ig-B7-H3 has an 88% of amino acid identity with mouse 2Ig-B7-H3. B7-H3 has an immunosuppressive function, which can reduce type I interferon (IFN) released from T cells and reduce cytotoxicity of NK cells.

B7-H3 proteins have limited expression in normal tissues (such as prostate, breast, placenta, liver, colon and lymphoid organs) but are abnormally expressed in most malignant tumors. B7-H3 expression can be detected in non-small-cell lung cancer cell lines and tumor tissues. B7-H3 mRNA and B7-H3 proteins are highly expressed in all six non-small-cell lung cancer cell lines and also expressed in a cell membrane and cytoplasm of cancer cells with an expression rate of about 73%. In the tumor tissues expressing B7-H3, the number of infiltrating lymphoid cells is significantly reduced and positively correlated with lymph node metastasis (Sun Y, Wang Y, Zhao J, et al. B7-H3 and B7-H4 expression in non-small-cell lung cancer[J]. Lung Cancer, 2006, 53(2): 143-151; Zhao Wenjian, Chen Chunyan, Sui Wenyan, et al. Advances in B7-H3 and its relationship with tumors[J]. Medical Recapitulate, 2009, 15(22): 3430-3433.).

Generally, B7-H3 overexpression in tumor cells is closely associated with reduced tumor-infiltrating lymphocytes, accelerated cancer progression and clinical outcomes of malignant tumors (nervous system tumor, melanoma, lung cancer, head and neck cancer, colorectal cancer, pancreatic cancer, prostate cancer, ovarian cancer, lung cancer and clear cell renal cell carcinoma). B7-H3 has become a potential target for cancer immunotherapy due to widespread expression in a variety of tumors. A B7-H3-specific monoclonal antibody (mAb) and an antibody-drug conjugate show anti-tumor activity against B7-H3-positive tumor cells in mouse xenograft models, and a phase I clinical trial shows a good safety profile (NCT01099644, NCT02381314 and NCT02982941). Since B7-H3 is highly expressed in tumor histiocytes but not or low expressed in normal histiocytes, B7-H3 is considered as a diagnostic marker for certain tumors. B7-H3 is closely related to biological characteristics of tumors and has become one of the hot targets for the treatment of malignant tumors.

A structure of human B7H3 is shown in FIG. 1. An extracellular structure of B7H3 is composed of two Ig-V domain+Ig-C2 domain in tandem with an almost identical sequence. A highly expressed alternative spliceosome lacks an intermediate moiety, and an extracellular region has only one Ig-V domain+Ig-C2 domain. Mouse B7H3 has only one IgV+IgC2 unit. A structure of Ig-V domain+Ig-C2 domain is similar to that of PD-L1. The four domains are linked mainly by flexible linker peptides and can swing freely. B7H3 is mainly expressed as a monomer, and homodimerization may occur in vitro. However, no protein with a homology of more than 30% with B7H3 is present in a human body.

SUMMARY

The present application is to provide an anti-B7H3 antibody and a use thereof. The antibody is used alone and/or in combination with other drugs for the treatment of cancers.

To achieve this, the present application adopts technical solutions described below.

In a first aspect, the present application provides an anti-B7H3 antigen-binding fragment. An amino acid sequence of CDR3 of a heavy chain variable region of the antigen-binding fragment is as shown in SEQ ID NO: 1, SEQ ID NO: 2, SEQ ID NO: 3 or SEQ ID NO: 4;

an amino acid sequence of CDR3 of a light chain variable region of the antigen-binding fragment is as shown in SEQ ID NO: 5, SEQ ID NO: 6, SEQ ID NO: 7 or SEQ ID NO: 8;

an amino acid sequence of CDR2 of the heavy chain variable region of the antigen-binding fragment is as shown in SEQ ID NO: 9, SEQ ID NO: 10, SEQ ID NO: 11 or SEQ ID NO: 12;

an amino acid sequence of CDR2 of the light chain variable region of the antigen-binding fragment is as shown in SEQ ID NO: 13, SEQ ID NO: 14, SEQ ID NO: 15 or SEQ ID NO: 16;

an amino acid sequence of CDR1 of the heavy chain variable region of the antigen-binding fragment is as shown in SEQ ID NO: 17, SEQ ID NO: 18, SEQ ID NO: 19 or SEQ ID NO: 20;

an amino acid sequence of CDR1 of the light chain variable region of the antigen-binding fragment is as shown in SEQ ID NO: 21, SEQ ID NO: 22, SEQ ID NO: 23 or SEQ ID NO: 24. Unless otherwise stated, positions of specific amino acid residues in an antibody variable region are numbered according to a Kabat numbering system.

According to the present application, a heavy chain variable region of an antigen-binding fragment of an anti-B7H3 antibody 26B6 includes CDR1 as shown in SEQ ID NO: 17, CDR2 as shown in SEQ ID NO: 9 and CDR3 as shown in SEQ ID NO: 1;

a light chain variable region includes CDR1 as shown in SEQ ID NO: 21, CDR2 as shown in SEQ ID NO: 13 and CDR3 as shown in SEQ ID NO: 5.

```
SEQ ID NO: 17:
GYAFTEY;

SEQ ID NO: 9:
NPNTGG;

SEQ ID NO: 1:
PYRDDGGFHWYFDV;

SEQ ID NO: 21:
SASSSVSYMQ;

SEQ ID NO: 13:
DTSKLTS;

SEQ ID NO: 5:
QQWSSNPLT.
```

The heavy chain variable region of the anti-B7H3 antibody 26B6 containing the above antigen-binding fragments includes an amino acid sequence as shown in SEQ ID NO: 25, and the light chain variable region includes an amino acid sequence as shown in SEQ ID NO: 26. A heavy chain variable region of humanized 26B6 includes an amino acid sequence as shown in SEQ ID NO: 27, and a light chain variable region includes an amino acid sequence as shown in SEQ ID NO: 28.

```
SEQ ID NO: 25 (26B6HV):
EVQLQQSGPELVKPGASVKISCKTSGYAFTEYTMHWVKQSQGKSLEWIG

GINPNTGGTTYNQKFNGKATLTVDRSSSTAYMELRSLTSEDSAVYYCTR

PYRDDGGFHWYFDVWGAGTAVTVSSAS;

SEQ ID NO: 26 (26B6LV):
QIVLTQSPAVMSTSPGEKVTMTCSASSSVSYMQWYQQKSGTSPKRWIYD

TSKLTSGVPARFSGSGSGTSYSLTISSMEAEDAATYYCQQWSSNPLTFG

AGTKLELKRADAAP;

SEQ ID NO: 27 (hz26B6HV):
EVQLVQSGAEVKKPGASVKVSCKASGYTFTEYTMHWVRQAPGQGLEWIG

GINPNTGGTTYNQKFNGRVTMTRDTSISTAYMELSSLRSEDTAVYYCTR

PYRDDGGFHWYFDVWGQGTLVTVSS;

SEQ ID NO: 28 (hz26B6LV):
EIVLTQSPATLSLSPGERATLSCSASSSVSYMQWYQQKPGLAPRLLIYD

TSKLTSGIPDRFSGSGSGTDFTLTISRLEPEDFAVYYCQQWSSNPLTFG

GGTKVEIKRTV.
```

According to the present application, a heavy chain variable region of an antigen-binding fragment of an anti-B7H3 antibody 6F7 includes CDR1 as shown in SEQ ID NO: 18, CDR2 as shown in SEQ ID NO: 10 and CDR3 as shown in SEQ ID NO: 2;

a light chain variable region includes CDR1 as shown in SEQ ID NO: 22, CDR2 as shown in SEQ ID NO: 14 and CDR3 as shown in SEQ ID NO: 6.

```
SEQ ID NO: 18:
GFTFTDY;

SEQ ID NO: 10:
RNKANGYT;

SEQ ID NO: 2:
DSHYRPFAY;

SEQ ID NO: 22:
KSSQSLLNSGNQNNYLT;

SEQ ID NO: 14:
LASTRDS;

SEQ ID NO: 6:
QNDYTYPLT.
```

The heavy chain variable region of the anti-B7H3 antibody 6F7 containing the above antigen-binding fragments includes an amino acid sequence as shown in SEQ ID NO: 29, and the light chain variable region includes an amino acid sequence as shown in SEQ ID NO: 30. A heavy chain variable region of humanized 6F7 includes an amino acid sequence as shown in SEQ ID NO: 31, and a light chain variable region includes an amino acid sequence as shown in SEQ ID NO: 32 or SEQ ID NO: 33.

```
SEQ ID NO: 29 (6F7HV):
EVKLVESGGGLVQPGGSLRLSCATSGFTFTDYYMSWVRQPPGKALEWLG
```

```
FIRNKANGYTTEYSASVKGRFTISSDDSQSILYLQMNTLRAEDSATYYC

ARDSHYRPFAYWGQGTLVTVSAAS;

SEQ ID NO: 30 (6F7LV):
DIQMTQSPSSLTVTAGEKVTMSCKSSQSLLNSGNQNNYLTWYQQKPGQP

PKLLIYLASTRDSGVPDRFTGSGSGTDFTLTISSVQAEDLAVYYCQNDY

TYPLTFGAGTKLELKRADAAP;

SEQ ID NO: 31 (hz6F7HV):
EVQLVESGGGLVQPGGSLRLSCAASGFTFTDYYMSWVRQAPGKGLEWVA

FIRNKANGYTTEYSASVKGRFTISRDDSKNSLYLQMNSLRAEDTAVYYC

ARDSHYRPFAYWGQGTLVTVSS;

SEQ ID NO: 32 (hz6F7LV1):
DIVMTQSPLSLPVTPGEPASISCKSSQSLLNSGNQNNYLTWYLQKPGQS

PQLLIYLASTRDSGVPDRFSGSGSGTDFTLKISRVEAEDVGVYYCQNDY

TYPLTFGGGTKVEIKRTV;

SEQ ID NO: 33 (hz6F7LV2):
DIVMTQSPDSLAVSLGERATINCKSSQSLLNSGNQNNYLTWYQQKPGQP

PKLLIYLASTRDSGVPDRFSGSGSGTDFTLTISSLQAEDVAVYYCQNDY

TYPLTFGGGTKVEIKRTV.
```

According to the present application, a heavy chain variable region of an antigen-binding fragment of an anti-B7H3 antibody 2B8 includes CDR1 as shown in SEQ ID NO: 19, CDR2 as shown in SEQ ID NO: 11 and CDR3 as shown in SEQ ID NO: 3;

a light chain variable region includes CDR1 as shown in SEQ ID NO: 23, CDR2 as shown in SEQ ID NO: 15 and CDR3 as shown in SEQ ID NO: 7.

```
SEQ ID NO: 19:
GYTFTDG;

SEQ ID NO: 11:
NTNSGN;

SEQ ID NO: 3:
GVFYYGYGAWFAY;

SEQ ID NO: 23:
RASKTISNYLA;

SEQ ID NO: 15:
SGSTLQS;

SEQ ID NO: 7:
QQHHEYPLT.
```

The heavy chain variable region of the anti-B7H3 antibody 2B8 containing the above antigen-binding fragments includes an amino acid sequence as shown in SEQ ID NO: 34, and the light chain variable region includes an amino acid sequence as shown in SEQ ID NO: 35. A heavy chain variable region of humanized 2B8 includes an amino acid sequence as shown in SEQ ID NO: 36, and a light chain variable region includes an amino acid sequence as shown in SEQ ID NO: 37.

```
SEQ ID NO: 34 (2B8HV):
QVQLQQSGPELVRPGVSVKISCKVSGYTFTDGAMHWVKRSHAKSLEWIG

IINTNSGNTNYNQKFQGKATMTVDKSSSTAYMELARLTSEDSAIYYCAR

GVFYYGYGAWFAYWGQGTLVTVSAAS;
```

5

-continued

```
SEQ ID NO: 35 (2B8LV):
DVQITQSPSYLTASPGETIIINCRASKTISNYLAWYQEKPGKTNKLLIY

SGSTLQSGIPSRFSGSGSDTDFTLTISSLEPEDFAMYYCQQHHEYPLTF

GAGTKLELKRADAAP;

SEQ ID NO: 36 (hz2B8HV):
QVQLVQSGAEVKKPGASVKVSCKVSGYTFTDGAMHWVRQAPGQGLEWIG

IINTNSGNTNYNQKFQGRVTMTRDTSISTAYMELSRLRSEDTAVYYCAR

GVFYYGYGAWFAYWGQGTLVTVSS;

SEQ ID NO: 37 (hz2B8LV):
DIQLTQSPSFLSASVGDRVTINCRASKTISNYLAWYQQKPGKAPKLLIY

SGSTLQSGVPSRFSGSGSGTDFTLTISSLQPEDFATYYCQQHHEYPLTF

GGGTKVEIKRTV.
```

According to the present application, a heavy chain variable region of an antigen-binding fragment of an anti-B7H3 antibody 23H1 includes CDR1 as shown in SEQ ID NO: 20, CDR2 as shown in SEQ ID NO: 12 and CDR3 as shown in SEQ ID NO: 4;

a light chain variable region includes CDR1 as shown in SEQ ID NO: 24, CDR2 as shown in SEQ ID NO: 16 and CDR3 as shown in SEQ ID NO: 8.

```
SEQ ID NO: 20:
GFTFTDY;

SEQ ID NO: 12:
RNKVNDYT;

SEQ ID NO: 4:
DSPYRPFAY;

SEQ ID NO: 24:
KSSQTLLNNGNQKNFLT;

SEQ ID NO: 16:
LASTRES;

SEQ ID NO: 8:
NDYTYPLT.
```

The heavy chain variable region of the anti-B7H3 antibody 23H1 containing the above antigen-binding fragments includes an amino acid sequence as shown in SEQ ID NO: 38, and the light chain variable region includes an amino acid sequence as shown in SEQ ID NO: 39.

```
SEQ ID NO: 38 (23H1HV):
EVKLVESGGGLVQPGGSLRLSCATSGFTFTDYYMSWVRQPPGKALEWLG

FIRNKVNDYTTEYSVSVKGRFTISRDNSQTILYLQMNTLRAEDSATYYC

ARDSPYRPFAYWGQGTLVTVSAAS;

SEQ ID NO: 39 (23H1LV):
DIVMTQSPSSLTVTAGENVTMSCKSSQTLLNNGNQKNFLTWYQQKPGQP

PKLLIYLASTRESGVPDRFTGSGSGTDFTLTISSVQAEDLAVYYCQNDY

TYPLTFGAGTKLELKRADAAP.
```

Preferably, the antibody further includes a constant region.

Preferably, an antibody molecule may be an N-terminal, internal or C-terminal modification, such as an oligomerization modification, a glycosylation modification or a modification of conjugation with a marker, thereby adjusting a function of the antibody.

According to the present application, antibody glycosylation can adjust the function of the antibody and affect a half-life, immunogenicity, antibody-dependent cell-mediated cytotoxicity (ADCC) and complement-dependent cytotoxicity (CDC) of the antibody. The antibody glycosylation is mainly related to factors such as an antibody sequence, an amino acid exposure site and a synthesis condition. According to types of glycosidic chains, protein glycosylation may be divided into four types, that is, hydroxyl of serine, threonine, hydroxylysine and hydroxyproline is used as a linkage point to form an —O-glycosidic bond type, an amide group of asparagine, α-amino of an N-terminal amino acid and ω-amino of lysine or arginine are used as linkage points to form an —N-glycosidic bond type, a free carboxyl group of an aspartic acid or glutamate is used as a linkage point to form a lipo-glycosidic bond type; and cysteine is used as a linkage point to form a glycopeptide bond.

In a second aspect, the present application provides a nucleic acid molecule. The nucleic acid molecule includes a DNA fragment for encoding the antigen-binding fragment and/or the antibody according to the first aspect.

In a third aspect, the present application provides an expression vector. The expression vector includes the nucleic acid molecule according to the second aspect.

In a fourth aspect, the present application provides a host cell. The host cell includes the expression vector according to the third aspect, and/or a genome of the host cell is integrated with the nucleic acid molecule according to the second aspect.

In a fifth aspect, the present application provides a method for preparing an antibody. The method includes the following steps:

(1) ligating an encoding nucleic acid of the antibody according to the first aspect to a plasmid, transferring into a competent cell and culturing, then selecting monoclonal cells for screening;

(2) extracting an expression vector of a screened positive clone, transferring into a host cell, culturing and collecting a supernatant, then separating and purifying to obtain the antibody.

As a preferred technical solution, the present application provides a method for preparing an antibody. The method includes the following steps:

transfecting host cells transiently or stably with an antibody secretion system containing a heavy chain (HC) expression vector and a light chain (LC) expression vector in a specific ratio, or with a single vector containing coding HC and LC sequences, wherein the host cells may be, for example, HEK 293 or CHO;

obtaining purified antibody from a cell culture supernatant by a conventional method, for example, for Fab fragments, filtering the culture supernatant with a MabSelect column (GE Healthcare) or a KappaSelect column (GE Healthcare) equilibrated by phosphate buffer (pH=7.4), and removing non-specific binding components of the columns by washing; eluting the bound antibody with pH gradient eluent (20 mM pH=7 Tris buffer to 10 mM pH=3.0 sodium citrate buffer, or pH=7.4 phosphate buffer to 100 mM pH=3.0 glycine buffer);

detecting the antibody through SDS-PAGE, and optionally further purifying;

concentrating and/or sterile filtering the antibody to remove soluble aggregates and multimers with conventional techniques, wherein conventional techniques includes size-exclusion chromatography, hydrophobic interaction chromatography, ion exchange chromatography, multimodal chromatography or hydroxyapatite chromatography;

after the step of chromatographic concentration, the purity of the antibody is greater than 95%, and a product of the high-purity antibody is frozen or lyophilized at −70° C.

In a sixth aspect, the present application provides a pharmaceutical composition. The pharmaceutical composition includes the antibody according to the first aspect.

Preferably, the pharmaceutical composition further includes an anti-tumor drug.

Preferably, the pharmaceutical composition further includes any one or a combination of at least two of a pharmaceutically acceptable carrier, a diluent or an excipient.

In a seventh aspect, the present application provides a use of the antigen-binding fragment and/or the antibody according to the first aspect, the nucleic acid molecule according to the second aspect, the expression vector according to the third aspect, the host cell according to the fourth aspect or the pharmaceutical composition according to the sixth aspect for preparing a tumor detection reagent and/or a tumor treatment drug.

Preferably, the tumor includes a tumor that is positive for B7H3 expression.

Preferably, the tumor includes any one or a combination of at least two of nervous system tumor, melanoma, lung cancer, head and neck cancer, colorectal cancer, pancreatic cancer, gastric cancer, kidney cancer, bladder cancer, prostate cancer, breast cancer, ovarian cancer or hepatocellular carcinoma.

The existing art has reported a diagnostic value of B7H3 in diseases such as primary liver cancer (Guo Haosu, Yang Yirong, Li Kai, He Kangli, Li Xingyue, Liu Hong; Diagnostic Significance of Serum CYFRA21-1 and sB7-H3 in Primary Liver Cancer[J]; China Journal of Modern Medicine.), esophageal squamous cell carcinoma (Sun Nan, Liu Xinbo, Cao Nana, Wang Ling; Expression and Clinical Significance of B7-H3 Gene in Peripheral Blood of Patients with Esophageal Squamous Cell Carcinoma[J]; Chinese Journal of Surgical Oncology; 2019 11(04): 247-250.), neuroblastoma (Liao Ru, Sun Xiaofei, Zhen Zijun, Wang Juan, Huang Dongsheng; Expression and Clinical Significance of B7H3 in Neuroblastoma Tissues[J]; Chinese Journal of Applied Clinical Pediatrics; 2019(11): 842-847.), colon cancer (Liang Qunying, Zhang Yuwen, Qiu Xiaodi; Expression of B7-H3 Protein in Colon Carcinoma and Clinical Pathological Significance[J]; Chinese Journal of Practical Medicine; 2018 45(15): 48-52.) and head and neck squamous cell carcinoma (Mao Liang, Fan Tengfei, Wu Lei, Yu Guangtao, Deng Weiwei, Chen Lei, Bu Linlin, Ma Sirui, Liu Bing, Bian Yansong, Ashok B Kulkarni, Zhang Wenfeng, Sun Zhijun; Selective Blocking of B7-H3 in Head and Neck Squamous Cell Carcinoma B7-H3 can Enhance Anti-tumor Immune Effect by Reducing Myeloid-derived Suppressor Cells[C]; Chinese Stomatological Association; 2017: 139.), and the anti-B7H3 antibody has a therapeutic effect on tumors that are positive for B7H3 expression. The anti-B7H3 antibodies 26B6, 6F7, 2B8 and 23H1 of the present application each have a significant binding ability to B7H3 and a broad application prospect in the diagnosis and treatment of tumors that are positive for B7H3 expression.

Compared with the existing art, the present application has the beneficial effects described below.

(1) The anti-B7H3 antibodies 26B6, 6F7, 2B8 and 23H1 of the present application each have the significant binding ability to B7H3 and can bind not only purified or free B7H3 proteins but also B7H3 proteins on a cell surface.

(2) After the antibody of the present application is humanized, an affinity between the antibody and B7H3 is further improved.

(3) The antibody and the humanized antibody of the present application each have an important application prospect in the treatment of B7H3-positive tumors.

DETAILED DESCRIPTION

Figure 1:
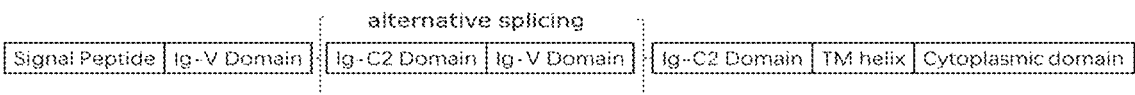
FIG. 1 is a structure diagram of human B7H3.

To further elaborate on the technical means adopted and effects achieved in the present application, the present application is further described below in conjunction with examples and drawings. It is to be understood that the specific examples set forth below are intended to explain the present application and not to limit the present application.

Experiments without specific techniques or conditions specified in the examples are conducted according to techniques or conditions described in the literature in the art or a product specification. The reagents or instruments used herein without manufacturers specified are conventional products commercially available from proper channels.

Example 1 Expression and Purification of Antibodies

This example provides four anti-B7H3 antibodies 26B6 (SEQ ID NOs: 25 and 26), 6F7 (SEQ ID NOs: 29 and 30), 2B8 (SEQ ID NOs: 34 and 35) and 23H1 (SEQ ID NOs: 38 and 39). A method for preparing the antibodies includes the steps described below.

Stable transfection was performed on host cells HEK 293 using an antibody secretion system containing an HC expression vector and an LC expression vector in specific proportions. After a period of culture, a cell culture supernatant was filtered using a MabSelect column (GE Healthcare) equilibrated by phosphate buffer (pH=7.4), and a non-specific binding component of the column was removed by washing. The bound antibody was eluted with pH gradient eluent (20 mM pH=7 Tris buffer to 10 mM pH=3.0 sodium citrate buffer). The obtained eluent was detected through SDS-PAGE and further purified. The purified product was concentrated and sterile filtered to remove soluble aggregates and multimers. After the step of concentration, the purity of the antibody was greater than 95%, and the high-purity antibodies 26B6, 6F7, 2B8 and 23H1 were frozen or lyophilized at −70° C.

Example 2 Affinity Test of Antibodies

Affinity detection was performed on the high-purity antibodies 26B6, 6F7, 2B8 and 23H1 prepared in Example 1 using a ForteBio affinity measurement method (P. Estep et al., High throughput solution-based measurement of antibody-antigen affinity and epitope binning. MAbs, 2013. 5(2): 270-278.), and control antibodies huM30 and Enoblituzumab (Eno) were set. huM30 is a humanized B7H3 antibody (CN103687945B) of Daiichi Sankyo Co., Ltd. in Japan, and DS-5573 is conducting a phase I clinical trial for the treatment of B7H3-positive solid tumors (NCT02192567). Enoblituzumab, a brand-new monoclonal antibody optimized by an immune molecule and aimed at a B7-H3 target, is developed by MacroGenics using an exclusive Fc optimization technology and has a unique antibody advantage and a therapeutic potential. With no such drug having been approved in the world, Enoblituzumab represents a leading B7-H3 antibody drug in the world.

Briefly, the antibody was loaded onto an AHQ sensor, and the sensor was equilibrated off-line in an assay buffer for 30 min and monitored online for 60 s for establishing a baseline. The antibody-loaded sensor was co-incubated with a 60 nM antigen B7H3 ECD-His for 5 min and transferred to the assay buffer, and a dissociation rate was measured after 5 min. Kinetic analysis was performed using a 1:1 binding model.

The results are shown in Table 1. Compared with the control antibodies huM30 and Eno on which clinical trials have been performed abroad, the 2B8, 26B8, 23H1 and 6F7 antibody screened in the present application have the same or better binding activity with human B7H3 ECD-his proteins.

TABLE 1

| Affinities of binding antibodies to human B7H3 ECD-His | | |
|---|---|---|
| Antigen | Antibody | Dissociation Equilibrium Constant KD (M) |
| human B7H3 ECD-His | huM30 | 3.46E−10 |
| | Eno | 7.73E−10 |
| | 2B8 | 3.23E−10 |
| | 26B6 | 4.35E−10 |
| | 23H1 | 6.85E−10 |
| | 6F7 | 5.37E−10 |

Example 3 Bindings of Antibodies to B7H3 on HEK293 Cells

In this example, the bindings of the antibodies prepared in Example 1 to B7H3 on the HEK293 cells were detected through flow cytometry. The steps are described below.

$5 \times 10^5$ HEK293 cells were resuspended with PBS+5% BSA and incubated for 30 min at 4° C. Different concentrations of antibody (1 µg/mL to 0.01 µg/mL, 10-fold gradient dilution) were added and incubated for 60 min at 4° C. After centrifugation and washing, a PBS+5% BSA solution containing an FITC-labeled secondary antibody (1:200, sigma, F9512) was added and incubated on ice for 30 min in the dark. Cells were washed three times before the flow cytometry analysis.

Control groups huM30, Eno, NC and Cell+secondary antibody were set.

Figure 2:
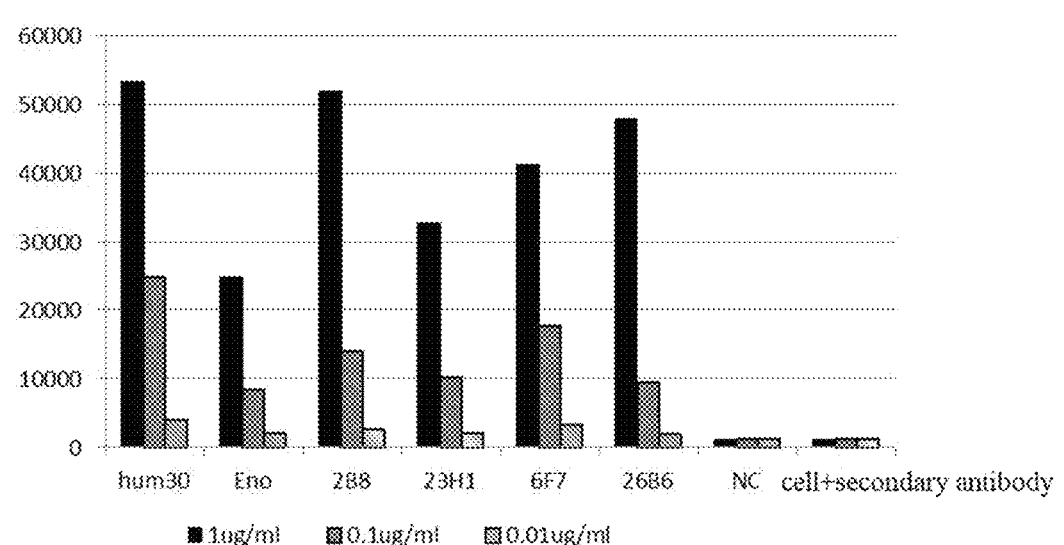
FIG. 2 illustrates that bindings of antibodies to B7H3 are detected through flow cytometry.

The results are shown in FIG. 2. Using the flow cytometry method, the control antibodies (huM30, Eno) and the 2B8, 26B8, 23H1 and 6F7 antibody were tested for their binding abilities to HEK293 B7H3 proteins at a final concentration of 1 µg/mL, 0.1 µg/mL and 0.01 µg/mL, respectively. Compared with the control antibodies, the 2B8, 26B6, 23H1 and 6F7 antibody each have the same or better binding ability to the HEK293 B7H3 proteins.

Example 4 ELISA Detection of Antibodies

Binding abilities of the antibodies 2B8, 26B8, 23H1 and 6F7 to extracellular fragments in different lengths of B7H3 proteins were detected through the indirect ELISA method. Five antigens (human B7H3-IgV-His, human B7H3-V1-C1-V2-His, human B7H3-IgC2, human B7H3-ECD-His and control proteins cyno-B7H3-His) were diluted to 0.2 µg/mL with a coating buffer, respectively, and added to a 96-well ELISA coating plate in 100 µL/well. After overnight incubation at 4° C., the wells were washed several times with a PBST solution and sealed with 1% BSA for 1 h at 37° C. 100 µL of the antibodies 2B8, 26B8, 23H1 and 6F7 with a final concentration of 0.5 µg/mL were added to each well, respectively, and incubated for 2 h at 37° C. After being washed five times with PBST, 100 µL of a diluted horseradish peroxidase (HRP)-labeled secondary antibody was added and incubated for 1 h at 37° C. After being washed five times with PBST, color development was performed with a chromogenic reagent for 20 min, and values were read on a microplate reader.

Figure 3:
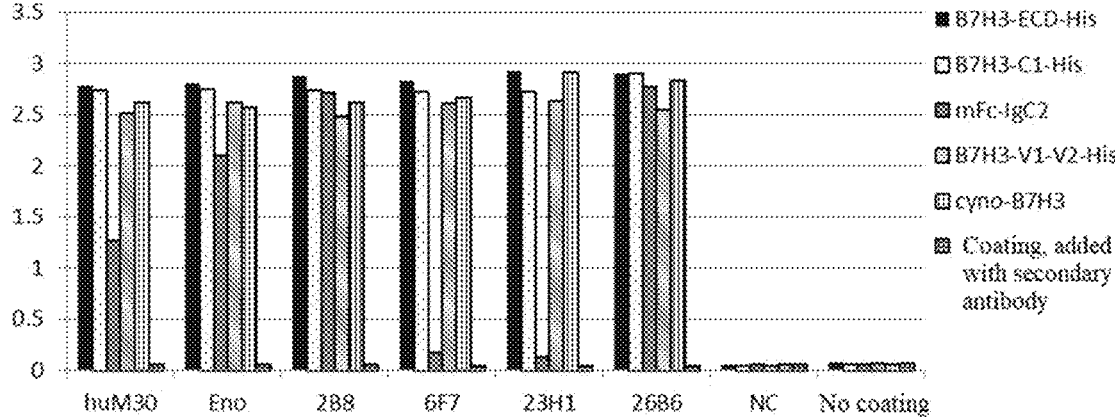
FIG. 3 illustrates that bindings of antibodies to B7H3 are detected through an enzyme-linked immunosorbent assay (ELISA).

The results are shown in FIG. 3. The 2B8 and 26B6 antibody and the control antibodies huM30 and Eno have similar binding features of extracellular fragments of the B7H3 proteins, except that the 23H1 and 6F7 antibody mainly bind to sites other than Ig-C2 regions of the extracellular fragments of the B7H3 proteins.

Example 5 Humanization of Antibodies

The antibodies 26B6, 6F7 and 2B8 prepared in Example 1 were humanized. Briefly, gene sequences of antibodies secreted by different hybridoma cells were compared with a gene sequence of a germline antibody from a human embryo to find a sequence with a high homology. An affinity of HLA-DR was analyzed and investigated, and a framework sequence of the germline from the human embryo with a low affinity was selected. Amino acid sequences of a variable region and a surround framework thereof were analyzed through molecular docking using a computer simulation technique. A spatial three-dimensional binding manner was investigated. Electrostatic force, van der Waals force, hydrophilicity, hydrophobicity and an entropy value were calculated, a key amino acid individual in the gene sequences of the antibodies secreted by each hybridoma cell was analyzed, which can interact with B7H3 and maintain a spatial framework. The key amino acid individual was grafted back to the selected gene framework of the germline from the human embryo, and based on this, an amino acid site of a framework region which must be retained was marked, a random primer was synthesized, a phage library was self-made, and a humanized antibody library was screened (A.

Pini et al., Design and use of a phage display library: human antibodies with subnanomolar affinity against a marker of angiogenesis eluted from a two-dimensional gel. Journal of Biological Chemistry, 1998. 273(34): 21769-21776).

hz26B6 (SEQ ID Nos: 27 and 28), hz6F7 (SEQ ID NOs: 31 to 33) and hz2B8 (SEQ ID NOs: 36 and 37) were obtained.

Example 6 Bindings of Humanized Antibodies to B7H3 on HEK293 Cells

In this example, the bindings of the humanized antibodies prepared in Example 5 to B7H3 on the HEK293 cells were detected through flow cytometry. The steps are described below.

$2\times10^5$ HEK293 cells were resuspended with PBS+5% BSA and incubated for 30 min at 4° C. Different concentrations of humanized antibody (5 μg/mL to 0.002286 μg/mL, 3-fold gradient dilution) were added and incubated for 60 min at 4° C. After centrifugation and washing, a PBS+5% BSA solution containing an FITC-labeled secondary antibody (1:200, sigma, F9512) was added and incubated on ice for 30 min in the dark. Cells were washed three times before the flow cytometry analysis. EC50 was calculated using GraphPad software.

Control groups huM30, Eno, NC and Cell+secondary antibody were set.

Figure 4:
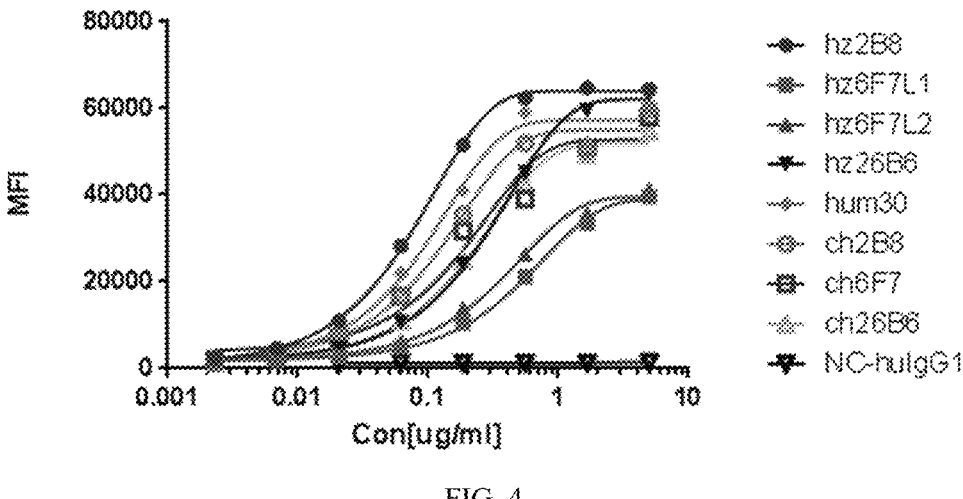
FIG. 4 illustrates that bindings of humanized antibodies to B7H3 are detected through flow cytometry.

The results are shown in Table 2 and FIG. 4. hz26B6 was bound to B7H3 in a dose-dependent manner with an EC50 value (n=1) of 0.3063 μg/mL, hz2B8 was bound to B7H3 in a dose-dependent manner with an EC50 value (n=1) of 0.07789 μg/mL, hz6F7L1 was bound to B7H3 in a dose-dependent manner with an EC50 value (n=1) of 0.6038 μg/mL, hz6F7L2 was bound to B7H3 in a dose-dependent manner with an EC50 value (n=1) of 0.4096 μg/mL, and huM30 was bound to B7H3 in a dose-dependent manner with an EC50 value (n=1) of 0.09737 μg/mL. A humanized h2B8 antibody shows a better EC50 result than huM30 when bound to human B7H3.

In addition, light and heavy chain variable regions of murine 2B8, 26B6 and 6F7 antibodies were ligated to a constant region of a human antibody to obtain chimeric antibodies ch2B8, ch26B6 and ch6F7, where ch2B8 was bound to B7H3 in a dose-dependent manner with an EC50 value (n=1) of 0.1315 μg/mL, ch26B6 was bound to B7H3 in a dose-dependent manner with an EC50 value (n=1) of 0.2323 μg/mL, and ch6F7 was bound to B7H3 in a dose-dependent manner with an EC50 value (n=1) of 0.2244 μg/mL.

Example 7 Differences in Affinities Between Antibodies and B7H3 and Affinities Between Humanized Antibodies and B7H3

In this example, the differences in the affinities between the antibodies and B7H3 and the affinities between the humanized antibodies and B7H3 were detected using a ForteBio affinity measurement method.

The results are shown in Table 3. Compared with the results in Table 1, the humanized h2B8 antibody has a better KD value than the unmodified antibody and is better than the control antibody huM30.

TABLE 3

| Affinities between humanized antibodies and human B7H3 ECD-His | | |
| --- | --- | --- |
| Antigen | Antibody | KD (M) |
| human B7H3 | huM30 | 2.77E−10 |
| ECD-His | h2B8 | 2.59E−10 |
| | h26B6 | 7.53E−10 |
| | h6F7 | 1.01E−09 |
| | h6F7H1L1 | 3.70E−08 |
| | h6F7H1L2 | 1.42E−08 |

Example 8 Membrane Protein Array (MAP) Verifies Binding Interactions Between Antibodies and B7H3

In this example, non-target binding interactions of the antibodies h26B6-scFv-hFc and h2B8-scFv-hFc were verified using the MAP. The steps are described below.

(1) Determination of Screening Conditions

Figure 5:
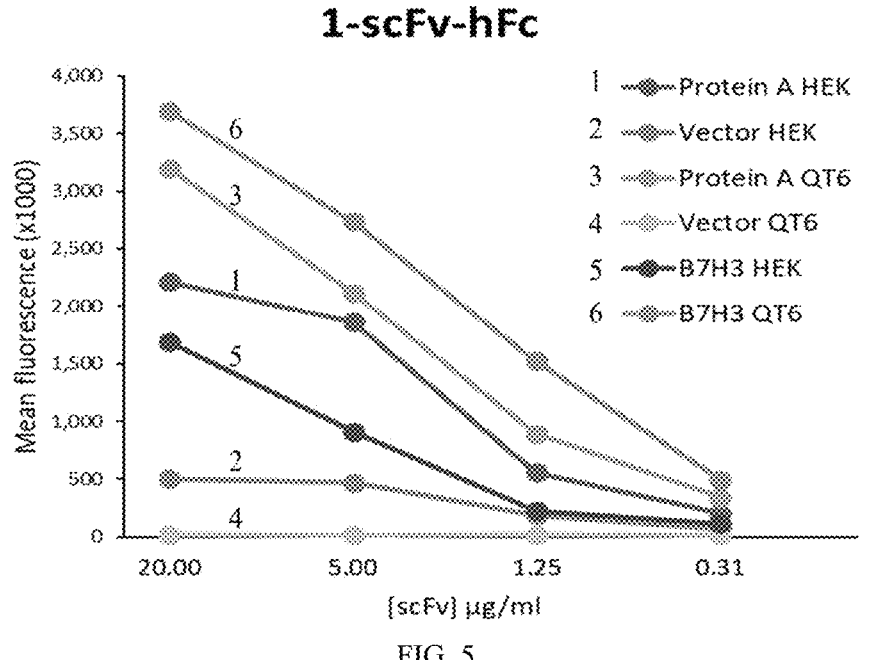
FIG. 5 illustrates suitable conditions for screening bindings of an antibody 1-scFv-hFc (hz26B6-scFv-hFc) through flow cytometry.
Figure 6:
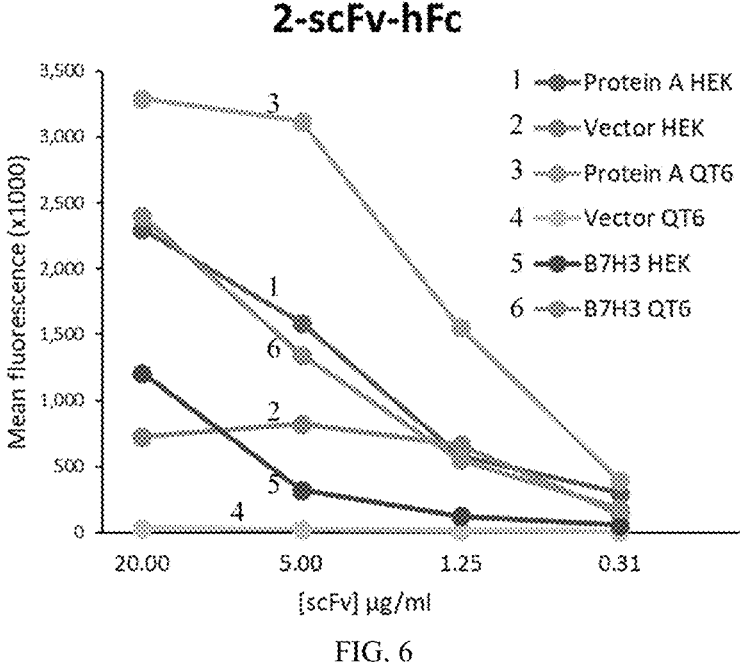
FIG. 6 illustrates suitable conditions for screening bindings of an antibody 2-scFv-hFc (hz2B8-scFv-hFc) through flow cytometry.

To optimize antibody detection conditions, HEK-293T cells and QT6 cells containing a plasmid containing a B7H3 antigen-encoding gene or an empty vector (pUC; negative control) were cultured in 384-well cell culture dishes. After culture for 24 h at 37° C. under 5% $CO_2$, each antibody to be detected was subjected to 4-fold dilution using a PBS solution containing 10% NGS, $Ca^{2+}$ and $Mg^{2+}$ and added in quadruplicate to transfected cells. The bindings of the antibodies to the cells were detected through high-throughput immunofluorescence flow cytometry (the conditions were the same as those described in Table 4). Dilution multiples of each antibody were determined using ForeCyt software (Intellicyt) according to a mean fluorescence intensity (MFI) value, and curves were plotted using Excel2017 (Microsoft) (as shown in FIGS. 5 and 6).

TABLE 2

| | Bindings of humanized antibodies to B7H3 | | | | | | | |
| --- | --- | --- | --- | --- | --- | --- | --- | --- |
| | h2B8 | h6F7H1L1 | h6F7H1L2 | h26B6 | huM30 | ch2B8 | ch6F7 | ch26B6 |
| EC50 (μg/mL) | 0.07789 | 0.6038 | 0.4096 | 0.3063 | 0.09737 | 0.1315 | 0.2323 | 0.2244 |

TABLE 4

| Experimental parameters for screening membrane protein array | | |
| --- | --- | --- |
| | 1-scFv-hFc | 2-scFc-hFc |
| Experimental Parameter | | |
| *Cells and Transfection* | | |
| Type of Cells | HEK-293T, QT6 | HEK-293T, QT6 |
| Positive Control Plasmid | Protein A, B7H3 | Protein A, B7H3 |
| Negative Control Plasmid | pUC | pUC |
| Incubation Condition | 36 h, 37° C., 5% $CO_2$ | 36 h, 37° C., 5% $CO_2$ |
| Blocking Buffer for Primary Antibody and Secondary Antibody | 10% goat serum (Sigma G6767) | 10% goat serum (Sigma G6767) |
| *Primary Antibody* | | |
| Name of Antibody (Ab) | | |
| Initial Concentration | 1 mg/ml | 1 mg/ml |
| Storage Condition | −20° C., 4° C. (after thawing) | −20° C., 4° C. (after thawing) |
| Lot Number | N/A | N/A |
| Validity Period | N/A | N/A |
| Source | Guangzhou Bio-gene Technology Co., Ltd. | Guangzhou Bio-gene Technology Co., Ltd. |
| Concentration | 4-fold dilution (in quadruplicate, starting concentration 20 µg/ml) | 4-fold dilution (in quadruplicate, starting concentration 20 µg/ml) |
| Incubation Time (Room Temperature) | 60 min | 60 min |
| *Secondary Antibody* | | |
| Target | Human IgG (Fc) | Human IgG (Fc) |
| Concentration | dilution in the buffer at 1:400 (3.75 µg/ml) | dilution in the buffer at 1:400 (3.75 µg/ml) |
| Incubation Time (Room Temperature) | 30 min | 30 min |
| Manufacturer | Jackson ImmunoResearch | Jackson ImmunoResearch |
| Cat # | 109-606-008 | 109-606-008 |
| Antibody ID | AlexaFluor ® 647-AffiniPure Goat Fab Anti-Human IgG (Fc) | AlexaFluor ® 647-AffiniPure Goat Fab Anti-Human IgG (Fc) |
| *Washing* | | |
| After Incubation with Primary Antibody | PBS (no $Ca^{2+}$, $Mg^{2+}$, Corning 46-013-CM diluted in deionized water) × 5 | PBS (no $Ca^{2+}$, $Mg^{2+}$, Corning 46-013-CM diluted in deionized water) × 5 |
| After Incubation with Secondary Antibody | PBS (no $Ca^{2+}$, $Mg^{2+}$, Corning 46-013-CM diluted in deionized water) × 2 | PBS (no $Ca^{2+}$, $Mg^{2+}$, Corning 46-013-CM diluted in deionized water) × 2 |
| *Operator and Device* | | |
| Liquid Treatment | PerkinElmer JANUS Automated Workstation | PerkinElmer JANUS Automated Workstation |
| Flow Cytometer | Intellicyt iQue | Intellicyt iQue |
| Detection Parameter | laser 640 nm, filtration 675/25 | laser 640 nm, filtration 675/25 |

(2) Screening of the MAP

A plasmid containing cDNA clones of 5344 membrane proteins (containing more than 90% of human membrane protein groups) was introduced into the QT6 cells and cultured in a 384-well cell culture plate, a unique cDNA was contained in each well, and the cells were cultured at 37° C. under 5% $CO_2$. After culture for 36 h, the cells were stripped using a cell stripper and placed in rows and columns into a new 384-well plate of a two-dimensional model, and the plate was arranged using a JANUS automated workstation. Each well in the model plate contained 48 different over-expressed protein components, and each protein was represented by a unique combination of two different wells. The antibodies to be detected were added to an MAP detection template at a pre-measured concentration, washed with 1×PBS and detected using the flow cytometer (see Table 5). All data of the flow cytometer was subjected to result processing using the ForeCyt software (Intellicyt).

Figure 7:
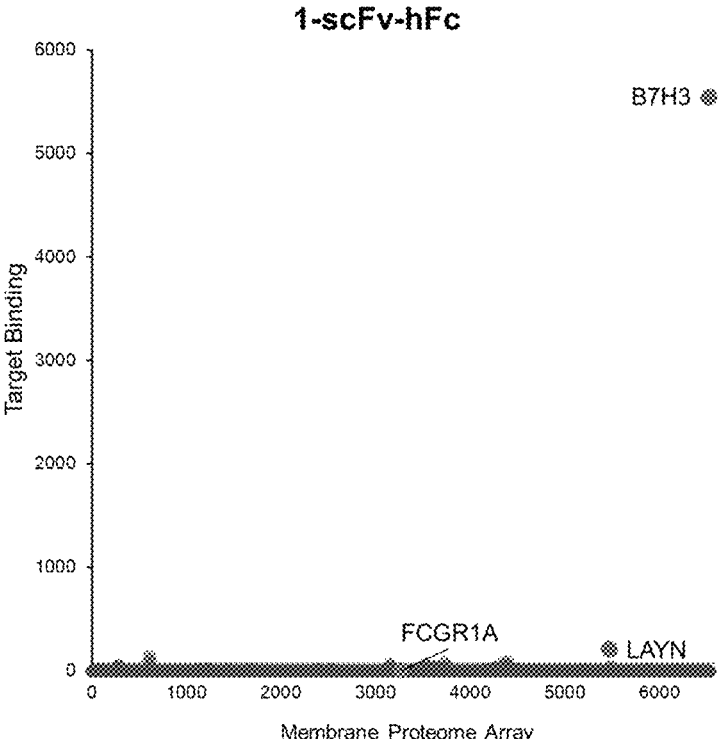
FIG. 7 is a binding target of an antibody 1-scFv-hFc.
Figure 8:
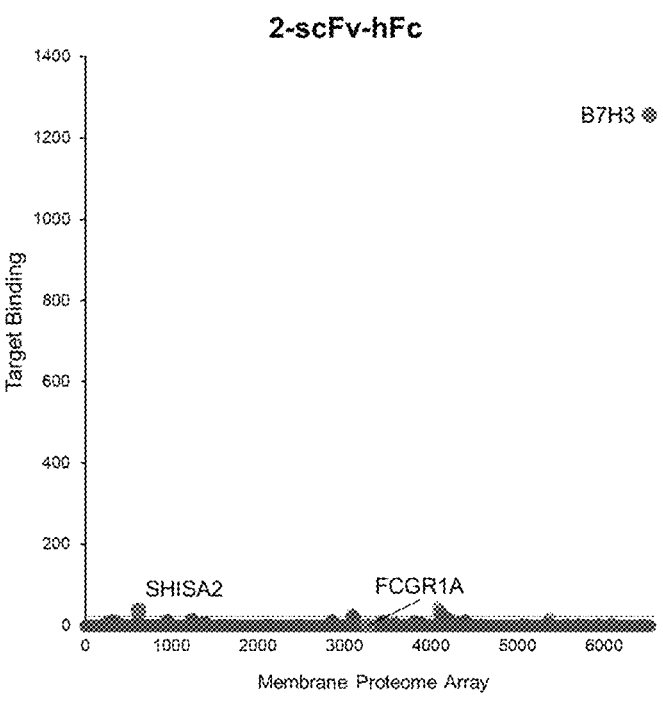
FIG. 8 is a binding target of an antibody 2-scFv-hFc.

To obtain signal values of the bindings of the antibodies to be detected to each protein in the MAP, the two-dimensional binding data was converted using a standard method. Briefly, a value of each well (representing a separate over-expressed protein) was converted to a radian and plotted as a standard target binding curve using a formula r·sin (2θ). Excel2017 (Microsoft) was used for all values and analyses (as shown in FIGS. 7 and 8).

The results are shown in Table 6. 1-scFv-hFc binds to B7H3 and LAYN proteins on a cytoplasmic membrane, and 2-scFc-hFc binds to B7H3 and SHISA2 proteins on the cytoplasmic membrane.

TABLE 5

| Experimental parameters for screening membrane protein array | | |
|---|---|---|
| | 1-scFv-hFc | 2-scFc-hFc |
| Experimental Parameter | | |
| Membrane Protein Array (MAP) | | |
| Type of Cells | QT6 | QT6 |
| Incubation Condition | 36 h, 37° C., 5% $CO_2$ | 36 h, 37° C., 5% $CO_2$ |
| Blocking buffer for primary antibody and secondary antibody | 10% goat serum (Sigma G6767) | 10% goat serum (Sigma G6767) |
| Primary Antibody | | |
| Name of Antibody (Ab) | | |
| Initial Concentration | 1 mg/ml | 1 mg/ml |
| Storage Condition | −20° C., 4° C. (after thawing) | −20° C., 4° C. (after thawing) |
| Lot Number | N/A | N/A |
| Validity Period | N/A | N/A |
| Source | Guangzhou Bio-gene Technology Co., Ltd. | Guangzhou Bio-gene Technology Co., Ltd. |
| Concentration | 20 μg/ml | 5 μg/ml |
| Incubation Time (Room Temperature) | 60 min | 60 min |
| Secondary Antibody | | |
| Target | Human IgG (Fc) | Human IgG (Fc) |
| Concentration | 1:400 (3.75 μg/ml) | 1:400 (3.75 μg/ml) |
| Incubation Time (Room Temperature) | 30 min | 30 min |
| Manufacturer | Jackson ImmunoResearch | Jackson ImmunoResearch |
| Cat # | 109-606-008 | 109-606-008 |
| Antibody ID | AlexaFluor ® 647-AffiniPure Goat Fab Anti-Human IgG (Fc) | AlexaFluor ® 647-AffiniPure Goat Fab Anti-Human IgG (Fc) |
| Washing | | |
| After Incubation with Primary Antibody | PBS (no $Ca^{2+}$, $Mg^{2+}$, Corning 46-013-CM diluted in deionized water) × 5 | PBS (no $Ca^{2+}$, $Mg^{2+}$, Corning 46-013-CM diluted in deionized water) × 5 |
| After Incubation with Secondary Antibody | PBS (no Ca2+, $Mg^{2+}$, Corning 46-013-CM diluted in deionized water) × 2 | PBS (no $Ca^{2+}$, $Mg^{2+}$, Corning 46-013-CM diluted in deionized water) × 2 |
| Operator and Device | | |
| Liquid Treatment | PerkinElmer JANUS Automated Workstation | PerkinElmer JANUS Automated Workstation |
| Flow Cytometer | Intellicyt iQue | Intellicyt iQue |
| Detection Parameter | laser 640 nm, filtration 647/25 | laser 640 nm, filtration 647/25 |

TABLE 6

| Verified targets of membrane proteins | | |
|---|---|---|
| Antibody | Target Gene (HGNC) | Protein Library |
| 1-scFv-hFc (hz26B6-scFv-hFc) | B7H3 LAYN | Q5ZPR3 Q6UX15 |
| 2-scFv-hFc (hz2B8-scFv-hFc) | B7H3 SHISA2 | Q5ZPR3 Q6UWI4 |

(3) Re-Verification of the Bindings of the Antibodies to the Target

Figure 9:
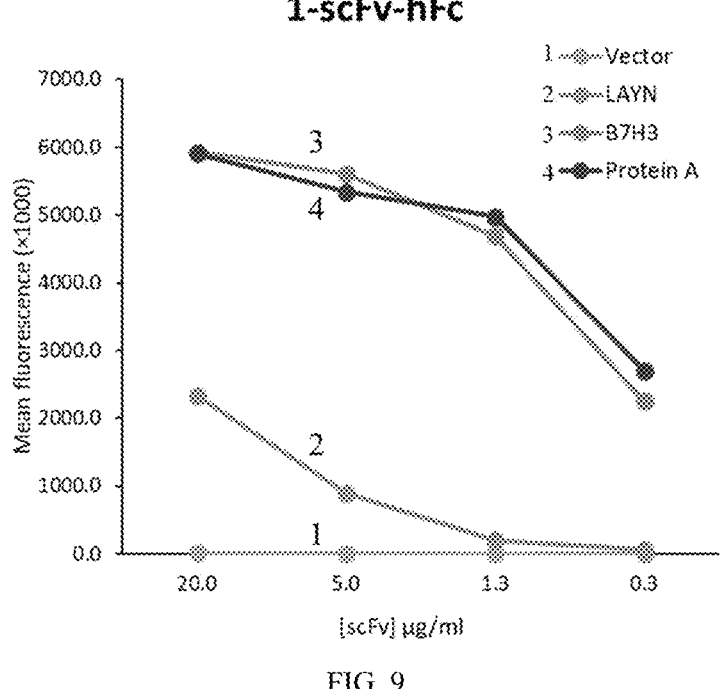
FIG. 9 illustrates that bindings of an antibody 1-scFv-hFc to B7H3 are detected through flow cytometry.
Figure 10:
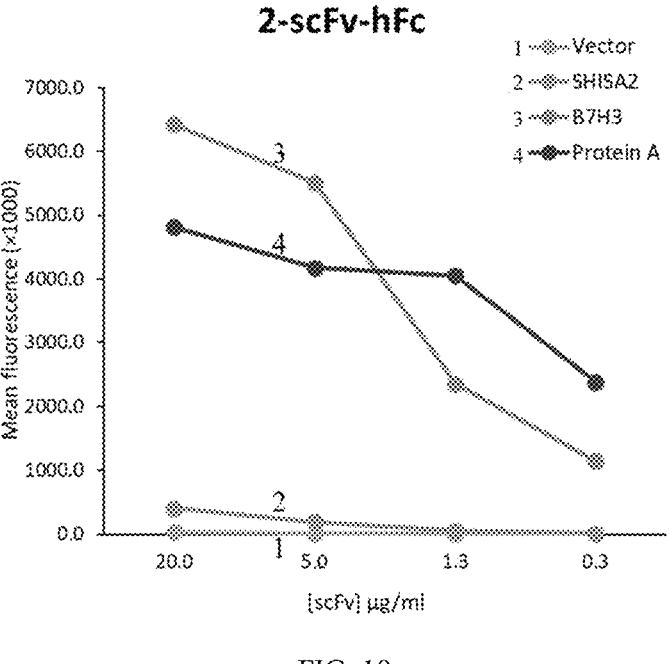
FIG. 10 illustrates that bindings of an antibody 2-scFv-hFc to B7H3 are detected through flow cytometry.

To verify the non-target binding interactions of the antibodies, plasmids encoding LAYN, SHISA2 and SEMA4B and an empty plasmid (pUC; negative control) were transfected into HEK 293T cells or QT6 cells and cultured in 384-well plates at 37° C. under 5% $CO_2$. After culture for 36 h, each antibody to be detected was subjected to 4-fold dilution and added to the transfected cells, and the bindings of the antibodies to the cells were detected using the high-throughput immunofluorescence flow cytometry (the conditions were the same as those described in Table 4). A dilution concentration of each antibody was measured using the ForeCyt software (Intellicyt), and a value of the dilution concentration was determined by an MFI value and plotted using Excel2017 (Microsoft) (as shown in FIGS. 9 and 10).

The results indicate that 1-scFv-hFc (hz26B6-scFv-hFc) and 2-scFv-hFc (hz2B8-scFv-hFc) can bind to B7H3 proteins without binding to other non-target proteins.

The applicant has stated that although the detailed method of the present application is described through the examples described above, the present application is not limited to the detailed method described above, which means that the implementation of the present application does not necessarily depend on the detailed method described above. It should be apparent to those skilled in the art that any improvements made to the present application, equivalent replacements of raw materials of the product of the present application, additions of adjuvant ingredients, selections of specific manners, etc., all fall within the protection scope and the disclosure scope of the present application.

What is claimed is:

1. An anti-B7H3 antibody or antigen-binding fragment thereof, comprising heavy chain variable domain CDRs: CDRH1, CDRH2, and CDRH3; and light chain variable domain CDRs: CDRL1, CDRL2, and CDRL3;
 wherein CDRH1 is selected from SEQ ID NOs: 17, 18, 19, or 20;
 wherein CDRH2 is selected from SEQ ID NOs: 9, 10, 11, or 12;
 wherein CDRH3 is selected from SEQ ID NOs: 1, 2, 3, or 4;
 wherein CDRL1 is selected from SEQ ID NOs: 21, 22, 23, or 24;
 wherein CDRL2 is selected from SEQ ID NOs: 13, 14, 15, or 16; and
 wherein CDRL3 is selected from SEQ ID NOs: 5, 6, 7, or 8.

2. The anti-B7H3 antibody or antigen-binding fragment thereof according to claim 1, wherein the CDRH1 is SEQ ID NO:17, the CDRH2 is SEQ ID NO:9, and the CDRH3 is SEQ ID NO:1; and
 the CDRL1 is SEQ ID NO:21, the CDRL2 is SEQ ID NO:13, and the CDRL3 is SEQ ID NO:5; or,
 the CDRH1 is SEQ ID NO:18, the CDRH2 is SEQ ID NO:10, and the CDRH3 is SEQ ID NO:2; and
 the CDRL1 is SEQ ID NO:22, the CDRL2 is SEQ ID NO:14, and the CDRL3 is SEQ ID NO:6; or,
 the CDRH1 is SEQ ID NO:19, the CDRH2 is SEQ ID NO:11, and the CDRH3 is SEQ ID NO:3; and the CDRL1 is SEQ ID NO:23, the CDRL2 is SEQ ID NO:15, and the CDRL3 is SEQ ID NO:7; or,
 the CDRH1 is SEQ ID NO:20, the CDRH2 is SEQ ID NO:12, and the CDRH3 is SEQ ID NO:4; and
 the CDRL1 is SEQ ID NO:24, the CDRL2 is SEQ ID NO:16, and the CDRL3 is SEQ ID NO:8.

3. The anti-B7H3 antibody or antigen-binding fragment thereof according to claim 1, comprising a heavy chain variable domain and a light chain variable domain;
 wherein the heavy chain variable domain is SEQ ID NO: 25, and the light chain variable domain is SEQ ID NO: 26;
 wherein the heavy chain variable domain is SEQ ID NO: 27, and the light chain variable domain is SEQ ID NO: 28;
 wherein the heavy chain variable domain is SEQ ID NO: 29, and the light chain variable domain is SEQ ID NO: 30;
 wherein the heavy chain variable domain is SEQ ID NO: 31, and the light chain variable domain is SEQ ID NO: 32 or SEQ ID NO: 33;
 wherein the heavy chain variable domain is SEQ ID NO: 34, and the light chain variable domain is SEQ ID NO: 35;
 wherein the heavy chain variable domain is SEQ ID NO: 36, and the light chain variable domain is SEQ ID NO: 37; or
 wherein the heavy chain variable domain is SEQ ID NO: 38, and the light chain variable domain is SEQ ID NO: 39.

4. A nucleic acid molecule, comprising a DNA fragment for encoding the antigen-binding fragment according to claim 1.

5. An expression vector, comprising the nucleic acid molecule according to claim 4.

6. A host cell, comprising the expression vector according to claim 5.

7. A method for preparing an antibody, comprising the following steps:

(1) ligating an encoding nucleic acid of the antigen-binding fragment according to claim 1 to a plasmid, transferring the plasmid into competent cells and culturing the competent cells, then selecting a positive clone by screening;

(2) extracting expression vectors from the positive clone, transferring the vectors into host cells, culturing the host cells and collecting a supernatant, then obtaining the antibody by separation and purification.

8. A pharmaceutical composition, comprising the antibody according to claim 3;

wherein the pharmaceutical composition further comprises any one or a combination of at least two of a pharmaceutically acceptable carrier, a diluent or an excipient.

9. A method comprising preparing a tumor detection reagent and/or a tumor treatment drug using the antigen-binding fragment according to claim 1;

wherein the tumor comprises a tumor that is positive for B7H3 expression; and wherein the tumor comprises any one or a combination of at least two of nervous system tumor, melanoma, lung cancer, head and neck cancer, colorectal cancer, pancreatic cancer, gastric cancer, kidney cancer, bladder cancer, prostate cancer, breast cancer, ovarian cancer or hepatocellular carcinoma.

10. The anti-B7H3 antibody according to claim 1, further comprising a constant region.

11. The anti-B7H3 antibody according to claim 1, wherein the antibody is modified with a glycosylation group.

\* \* \* \* \*